US009593274B2

(12) United States Patent
Fukushima

(10) Patent No.: US 9,593,274 B2
(45) Date of Patent: Mar. 14, 2017

(54) WORKING MEDIUM AND HEAT CYCLE SYSTEM

(71) Applicant: ASAHI GLASS COMPANY, LIMITED, Chiyoda-ku (JP)

(72) Inventor: Masato Fukushima, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/084,016

(22) Filed: Nov. 19, 2013

(65) Prior Publication Data
US 2014/0077122 A1    Mar. 20, 2014

Related U.S. Application Data

(63) Continuation of application No. PCT/JP2012/062842, filed on May 18, 2012.

(30) Foreign Application Priority Data

May 19, 2011 (JP) ................. 2011-112415

(51) Int. Cl.
C09K 5/04 (2006.01)
F25B 9/00 (2006.01)

(52) U.S. Cl.
CPC ............. C09K 5/044 (2013.01); C09K 5/045 (2013.01); F25B 9/002 (2013.01); *C09K 2205/12* (2013.01); *C09K 2205/126* (2013.01)

(58) Field of Classification Search
CPC ............. C09K 5/045; C09K 2205/126; C09K 2205/122; C09K 5/044; C10M 105/36
See application file for complete search history.

(56) References Cited

U.S. PATENT DOCUMENTS

| 2010/0154444 A1 | 6/2010 | Hulse et al. |
| 2010/0181524 A1* | 7/2010 | Elsheikh ................ C08F 2/42 |
| | | 252/78.1 |
| 2011/0057146 A1* | 3/2011 | Kaneko et al. ............... 252/68 |
| 2012/0215037 A1* | 8/2012 | Sun et al. .................... 570/157 |

(Continued)

FOREIGN PATENT DOCUMENTS

| CN | 103517963 A | 1/2014 |
| JP | 2010-531927 | 9/2010 |

(Continued)

OTHER PUBLICATIONS

International Search Report issued Jul. 3, 2012 in PCT/JP2012/062842 filed May 18, 2012.

*Primary Examiner* — John Hardee

(74) *Attorney, Agent, or Firm* — Oblon, McClelland, Maier & Neustadt, L.L.P.

(57) ABSTRACT

To provide a working medium for heat cycle, of which combustibility is suppressed, which has less influence over the ozone layer, which has less influence over global warming and which provides a heat cycle system excellent in the cycle performance (efficiency and capacity), and a heat cycle system, of which the safety is secured, and which is excellent in the cycle performance (efficiency and capacity).

A working medium for heat cycle comprising 1-chloro-2,3,3,3-tetrafluoropropene is employed for a heat cycle system (such as a Rankine cycle system, a heat pump cycle system, a refrigerating cycle system 10 or a heat transport system).

15 Claims, 2 Drawing Sheets

(56) References Cited

U.S. PATENT DOCUMENTS

2012/0292556 A1* 11/2012 Van Horn .......... C10M 171/008
　　　　　　　　　　　　　　　　　　　　　　252/68

FOREIGN PATENT DOCUMENTS

| WO | 2008/054778 | 5/2008 |
| WO | 2010/074254 | 7/2010 |
| WO | 2010/077898 | 7/2010 |

* cited by examiner

WORKING MEDIUM AND HEAT CYCLE SYSTEM

TECHNICAL FIELD

The present invention relates to a working medium and a heat cycle system employing the working medium.

BACKGROUND ART

Heretofore, as a working medium for heat cycle such as a coolant for a refrigerator, a coolant for an air conditioner, a working fluid for power generation system (such as exhaust heat recovery power generation), a working medium for a latent heat transport apparatus (such as a heat pipe) or a secondary cooling medium, a chlorofluorocarbon (CFC) such as chlorotrifluoromethane or dichlorodifluoromethane or a hydrochlorofluorocarbon (HCFC) such as chlorodifluoromethane has been used. However, influences of CFCs and HCFCs over the ozone layer in the stratosphere have been pointed out, and their use are regulated at present.

Accordingly, as a working medium for heat cycle, a hydrofluorocarbon (HFC) which has less influence over the ozone layer, such as difluoromethane (HFC-32), tetrafluoroethane or pentafluoroethane, has been used. However, it is pointed out that HFCs may cause global warming. Accordingly, development of a working medium for heat cycle which has less influence over the ozone layer and has a low global warming potential is an urgent need.

For example, 1,1,1,2-tetrafluoroethane (HFC-134a) used as a coolant for an automobile air conditioner has a global warming potential so high as 1,430 (100 years). Further, in an automobile air conditioner, the coolant is highly likely to leak out to the air e.g. from a connection hose or a bearing.

As a coolant which replaces HFC-134a, carbon dioxide and 1,1-difluoroethane (HFC-152a) having a global warming potential of 124 (100 years) which is low as compared with HFC-134a, have been studied.

However, with carbon dioxide, the equipment pressure tends to be extremely high as compared with HFC-134a, and accordingly there are many problems to be solved in application to all the automobiles. HFC-152a has a range of inflammability, and has a problem for securing the safety.

As a working medium for heat cycle, of which combustibility is suppressed, which has less influence over the ozone layer and has less influence over global warming, a hydrochlorofluoroolefin (HCFO) such as hydrochlorofluoropropene or a chlorofluoroolefin (CFO), having a high proportion of halogen which suppresses combustibility and having a carbon-carbon double bond which is easily decomposed by OH radicals in the air, is conceivable.

As the hydrochlorofluoropropene, for example, 1-chloro-3,3,3-trifluoropropene (E) (HCFO-1233zd(E)) has been known (Patent Document 1).

However, in a case where HCFO-1233zd(E) is used as a working medium for heat cycle, it is insufficient in the cycle performance (capacity).

PRIOR ART DOCUMENTS

Patent Documents

Patent Document 1: WO2010/077898

DISCLOSURE OF INVENTION

Technical Problem

The present invention provides a working medium for heat cycle, of which combustibility is suppressed, which has less influence over the ozone layer, which has less influence over global warming and which provides a heat cycle system excellent in the cycle performance (efficiency and capacity), and a heat cycle system, of which the safety is secured, and which is excellent in the cycle performance (efficiency and capacity).

Solution to Problem

The present invention provides a working medium for heat cycle (hereinafter sometimes referred to as working medium), which comprises 1-chloro-2,3,3,3-tetrafluoropropene (hereinafter sometimes referred to as HCFO-1224yd).

The working medium of the present invention preferably further contains a hydrocarbon.

The working medium of the present invention preferably further contains a HFC.

The working medium of the present invention preferably further contains a hydrofluoroolefin (HFO).

The heat cycle system of the present invention employs the working medium of the present invention.

Advantageous Effects of Invention

The working medium of the present invention, which comprises HCFO-1224yd having a high proportion of halogen, has combustibility suppressed. Further, since it comprises HCFO-1224yd having a carbon-carbon double bond which is easily decomposed by OH radicals in the air, it has less influence over the ozone layer and has less influence over global warming. Further, since it comprises HCFO-1224yd, it provides a heat cycle system which is excellent in the cycle performance (efficiency and capacity).

The heat cycle system of the present invention, which employs the working medium of the present invention of which combustibility is suppressed, has safety secured.

Further, since it employs the working medium of the present invention excellent in the thermodynamic properties, it is excellent in the cycle performance (efficiency and capacity). Further, due to excellent efficiency, a reduction in the power consumption will be attained, and due to excellent capacity, downsizing of a system can be achieved.

DESCRIPTION OF EMBODIMENTS

<Working Medium>

Figure 1:
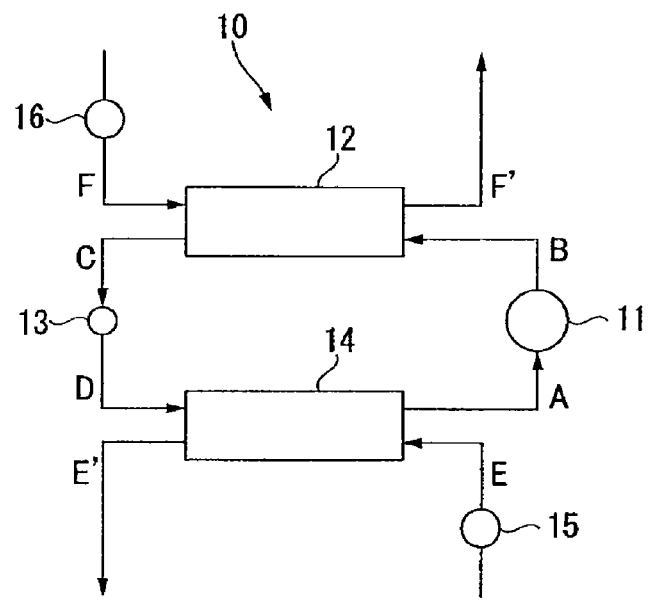
FIG. 1 is a schematic construction view illustrating an example of a refrigerating cycle system.

The working medium of the present invention comprises 1-chloro-2,3,3,3-tetrafluoropropene.

The working medium of the present invention may contain, as the case requires, another working medium which will be gasified or liquefied together with CFO1224yd, such as a hydrocarbon, a HFC, or a HFO. Further, the working medium of the present invention may be used in combination with a component other than the working medium, used together with the working medium (hereinafter, a composition containing the working medium and a component other than the working medium will be referred to as a working medium-containing composition). The component other than the working medium may, for example, be a lubricating oil, a stabilizer, a leak detecting substance, a desiccating agent or other additives.

The content of HCFO-1224yd is preferably at least 60 mass %, more preferably at least 70 mass %, further preferably at least 80 mass %, particularly preferably 100 mass % in the working medium (100 mass %).
(Hydrocarbon)

The hydrocarbon is a working medium component which improves solubility of the working medium in a mineral lubricating oil.

The hydrocarbon has preferably from 2 to 5 carbon atoms, and may be linear or branched.

The hydrocarbon is specifically preferably propane, propylene, cyclopropane, butane, isobutane, pentane or isopentane, particularly preferably propane, butane or isobutane.

The hydrocarbons may be used alone or in combination of two or more.

The content of the hydrocarbon is preferably from 1 to 40 mass %, more preferably from 2 to 10 mass %, in the working medium (100 mass %). When the content of the hydrocarbon is at least 1 mass %, the solubility of the lubricating oil in the working medium will sufficiently be improved. When the content of the hydrocarbon is at most 40 mass %, an effect to suppress combustibility of the working medium will be obtained.
(HFC)

The HFC is a working medium component which improves the cycle performance (capacity) of a heat cycle system.

The HFC is preferably a HFC which has less influence over the ozone layer and which has less influence over global warming.

The HFC has preferably from 1 to 5 carbon atoms, and may be linear or branched.

The HFC may, for example, be specifically difluoromethane, difluoroethane, trifluoroethane, tetrafluoroethane, pentafluoroethane, pentafluoropropane, hexafluoropropane, heptafluoropropane, pentafluorobutane or heptafluorocyclopentane. Among them, particularly preferred is difluoromethane (HFC-32), 1,1-difluoroethane (HFC-152a), 1,1,2,2-tetrafluoroethane (HFC-134), 1,1,1,2-tetrafluoroethane (HFC-134a) or pentafluoroethane (HFC-125), which has less influence over the ozone layer and which has less influence over global warming.

HFCs may be used alone or in combination of two more.

The content of the HFC in the working medium (100 mass %) is preferably from 1 to 99 mass %, more preferably from 1 to 40 mass %. For example, in a case where the HFC is HFC-134a, the refrigerating capacity will be improved without a remarkable decrease of the coefficient of performance, within a content range of from 1 to 99 mass %. In the case of HFC-245fa, the coefficient of performance and the refrigerating capacity will be improved within a content range of from 1 to 40 mass %. In the case of HFC-125, the refrigerating capacity will remarkably be improved without a remarkable decrease of the coefficient of performance, within a content range of from 1 to 40 mass %. In the case of HFC-32, the refrigerating capacity will remarkably be improved without a decrease of the coefficient of performance, within a content range of from 1 to 20 mass %. In the case of HFC-152a, the refrigerating capacity will remarkably be improved without a decrease of the coefficient of performance, within a content range of from 1 to 99 mass %.

The HFC content can be controlled depending upon the required properties of the working medium.
(HFO)

The HFO is a working medium component which improves the cycle performance (capacity) of a heat cycle system.

As the HFO, preferred is a HFO which has less influence over the ozone layer and which has less influence over global warming.

The HFO has preferably from 2 to 5 carbon atoms, and may be linear or branched.

The HFO may, for example, be specifically difluoroethylene, trifluoroethylene, trifluoropropylene, tetrafluoropropylene or pentafluoropropylene. Among them, particularly preferred is 1,1-difluoroethylene (HFO-132a), 1,2-difluoroethylene (HFO-1132) or 1,1,2-trifluoroethylene (HFO-1123), which has less influence over the ozone layer and which has less influence over global warming.

As HFO-1132, E isomer and Z isomer are present, and either of them may be used, or a mixture thereof may be used.

The HFOs may be used alone or in combination of two or more.

The content of the HFO is preferably from 1 to 99 mass %, more preferably from 1 to 40 mass % in the working medium (100 mass %). When the content of the HFO is from 1 to 40 mass %, it is possible to provide a heat cycle system excellent in the cycle performance (efficiency and capacity), as compared with a working medium comprising HCFO-1224yd.
(Lubricating Oil)

As the lubricating oil to be used for the working medium-containing composition, a known lubricating oil used for the heat cycle system may be used.

The lubricating oil may, for example, be an oxygen-containing synthetic oil (such as an ester lubricating oil or an ether lubricating oil), a fluorinated lubricating oil, a mineral oil or a hydrocarbon synthetic oil.

The ester lubricating oil may, for example, be a dibasic acid ester oil, a polyol ester oil, a complex ester oil or a polyol carbonate oil.

The dibasic acid ester oil is preferably an ester of a $C_{5-10}$ dibasic acid (such as glutaric acid, adipic acid, pimelic acid, suberic acid, azelaic acid or sebacic acid) with a $C_{1-15}$ monohydric alcohol which is linear or has a branched alkyl group (such as methanol, ethanol, propanol, butanol, pentanol, hexanol, heptanol, octanol, nonanol, decanol, undecanol, dodecanol, tridecanol, tetradecanol or pentadecanol). Specifically, ditridecyl glutarate, di(2-ethylhexyl) adipate, diisodecyl adipate, ditridecyl adipate or di(3-ethylhexyl) sebacate may, for example, be mentioned.

The polyol ester oil is preferably an ester of a diol (such as ethylene glycol, 1,3-propanediol, propylene glycol, 1,4-butanediol, 1,2-butanediol, 1,5-pentadiol, neopentyl glycol, 1,7-heptanediol or 1,12-dodecanediol) or a polyol having from 3 to 20 hydroxy groups (such as trimethylolethane, trimethylolpropane, trimethylolbutane, pentaerythritol, glycerol, sorbitol, sorbitan or sorbitol/glycerin condensate) with a $C_{6-20}$ fatty acid (such as a linear or branched fatty acid such as hexanoic acid, heptanoic acid, octanoic acid, nonanoic acid, decanoic acid, undecanoic acid, dodecanoic acid, eicosanoic acid or oleic acid, or a so-called neo acid having a quaternary a carbon atom).

The polyol ester oil may have a free hydroxy group.

The polyol ester oil is preferably an ester (such as trimethylolpropane tripelargonate, pentaerythritol 2-ethylhexanoate or pentaerythritol tetrapelargonate) of a hindered alcohol (such as neopentyl glycol, trimethylolethane, trimethylolpropane, trimethylolbutane or pentaerythritol).

The complex ester oil is an ester of a fatty acid and a dibasic acid, with a monohydric alcohol and a polyol. The fatty acid, the dibasic acid, the monohydric alcohol and the polyol may be as defined above.

The polyol carbonate oil is an ester of carbonic acid with a polyol.

The polyol may be the above-described diol or the above-described polyol. Further, the polyol carbonate oil may be a ring-opening polymer of a cyclic alkylene carbonate.

The ether lubricating oil may be a polyvinyl ether oil or a polyoxyalkylene lubricating oil.

The polyvinyl ether oil may be one obtained by polymerizing a vinyl ether monomer such as an alkyl vinyl ether, or a copolymer obtained by copolymerizing a vinyl ether monomer and a hydrocarbon monomer having an olefinic double bond.

The vinyl ether monomers may be used alone or in combination of two or more.

The hydrocarbon monomer having an olefinic double bond may, for example, be ethylene, propylene, various forms of butene, various forms of pentene, various forms of hexene, various forms of heptene, various forms of octene, diisobutylene, triisobutylene, styrene, α-methylstyrene or alkyl-substituted styrene. The hydrocarbon monomers having an olefinic double bond may be used alone or in combination of two or more.

The polyvinyl ether copolymer may be either of a block copolymer and a random copolymer.

The polyvinyl ethers may be used alone or in combination of two or more.

The polyoxyalkylene lubricating oil may, for example, be a polyoxyalkylene monool, a polyoxyalkylene polyol, an alkyl ether of a polyoxyalkylene monool or a polyoxyalkylene polyol, or an ester of a polyoxyalkylene monool or a polyoxyalkylene polyol. The polyoxyalkylene monool or the polyoxyalkylene polyol may be one obtained by e.g. a method of subjecting a $C_{2-4}$ alkylene oxide (such as ethylene oxide or propylene oxide) to ring-opening addition polymerization to an initiator such as water or a hydroxy group-containing compound in the presence of a catalyst such as an alkali hydroxide. Further, one molecule of the polyoxyalkylene chain may contain single oxyalkylene units or two or more types of oxyalkylene units. It is preferred that at least oxypropylene units are contained in one molecule.

The initiator may, for example, be water, a monohydric alcohol such as methanol or butanol, or a polyhydric alcohol such as ethylene glycol, propylene glycol, pentaerythritol or glycerol.

The polyoxyalkylene lubricating oil is preferably an alkyl ether or an ester of a polyoxyalkylene monool or polyoxyalkylene polyol. Further, the polyoxyalkylene polyol is preferably a polyoxyalkylene glycol. Particularly preferred is an alkyl ether of a polyoxyalkylene glycol having the terminal hydroxy group of the polyoxyalkylene glycol capped with an alkyl group such as a methyl group, which is called a polyglycol oil.

The fluorinated lubricating oil may, for example, be a compound having hydrogen atoms of a synthetic oil (such as the after-mentioned mineral oil, poly-α-olefin, alkylbenzene or alkylnaphthalene) substituted by fluorine atoms, a perfluoropolyether oil or a fluorinated silicone oil.

The mineral oil may, for example, be a naphthene mineral oil or a paraffin mineral oil obtained by purifying a lubricating oil fraction obtained by atmospheric distillation or vacuum distillation of crude oil by a purification treatment (such as solvent deasphalting, solvent extraction, hydrocracking, solvent dewaxing, catalytic dewaxing, hydrotreating or clay treatment) optionally in combination.

The hydrocarbon synthetic oil may, for example, be a poly-α-olefin, an alkylbenzene or an alkylnaphthalene.

The lubricating oils may be used alone or in combination of two or more.

The content of the lubricating oil is not limited within a range not to remarkably decrease the effects of the present invention, varies depending upon e.g. the application and the form of a compressor, and is preferably from 10 to 100 parts by mass, more preferably from 20 to 50 parts by mass based on the working medium (100 parts by mass).

(Stabilizer)

The stabilizer to be used for the working medium-containing composition is a component which improves the stability of the working medium against heat and oxidation.

The stabilizer may, for example, be an oxidation resistance-improving agent, a heat resistance-improving agent or a metal deactivator.

The oxidation resistance-improving agent and the heat resistance-improving agent may, for example, be N,N'-diphenylphenylenediamine, p-octyldiphenylamine, p,p'-dioctyldiphenylamine, N-phenyl-1-naphthyamine, N-phenyl-2-naphthylamine, N-(p-dodecyl)phenyl-2-naphthylamine, di-1-naphthylamine, di-2-naphthylamine, N-alkylphenothiazine, 6-(t-butyl)phenol, 2,6-di-(t-butyl)phenol, 4-methyl-2,6-di-(t-butyl)phenol or 4,4'-methylenebis(2,6-di-t-butylphenol). The oxidation resistance-improving agents and the heat resistance-improving agents may be used alone or in combination of two or more.

The metal deactivator may, for example, be imidazole, benzimidazole, 2-mercaptobenzothiazole, 2,5-dimercaptothiadiazole, salicylysine-propylenediamine, pyrazole, benzotriazole, tritriazole, 2-methylbenzamidazole, 3,5-dimethylpyrazole, methylenebis-benzotriazole, an organic acid or an ester thereof, a primary, secondary or tertiary aliphatic amine, an amine salt of an organic acid or inorganic acid, a heterocyclic nitrogen-containing compound, an amine salt of an alkyl phosphate, or a derivative thereof.

The content of the stabilizer is not limited within a range not to remarkably decrease the effects of the present invention, and is preferably at most 5 mass %, more preferably at most 1 mass % in the working medium-containing composition (100 mass %).

(Leak Detecting Substance)

The leak detecting substance to be used for the working medium-containing composition may, for example, be an ultraviolet fluorescent dye, an odor gas or an odor masking agent.

The ultraviolet fluorescent dye may be known ultraviolet fluorescent dyes as disclosed in e.g. U.S. Pat. No. 4,249,412, JP-A-10-502737, JP-A-2007-511645, JP-A-2008-500437 and JP-A-2008-531836.

The odor masking agent may be known perfumes as disclosed in e.g. JP-A-2008-500437 and JP-A-2008-531836.

In a case where the leak detecting substance is used, a solubilizing agent which improves the solubility of the leak detecting substance in the working medium may be used.

The solubilizing agent may be ones as disclosed in e.g. JP-A-2007-511645, JP-A-2008-500437 and JP-A-2008-531836.

The content of the leak detecting substance is not particularly limited within a range not to remarkably decrease the effects of the present invention, and is preferably at most 2 mass %, more preferably at most 0.5 mass % in the working medium-containing composition (100 mass %).
(Other Compound)

The working medium of the present invention and the working medium-containing composition may contain a $C_{1-4}$ alcohol or a compound used as a conventional working medium, coolant or heat transfer medium (hereinafter the alcohol and the compound will generally be referred to as other compound).

As such other compound, the following compounds may be mentioned.

Fluorinated ether: Perfluoropropyl methyl ether ($C_3F_7OCH_3$), perfluorobutyl methyl ether ($C_4F_9OCH_3$), perfluorobutyl ethyl ether ($C_4F_9OC_2H_5$), 1,1,2,2-tetrafluoroethyl-2,2,2-trifluoroethyl ether ($CF_2HCF_2OCH_2CF_3$), manufactured by Asahi Glass Company, Limited, AE-3000), etc.

The content of such other compound is not limited within a range not to remarkably decrease the effects of the present invention, and is preferably at most 30 mass %, more preferably at most 20 mass %, particularly preferably at most 15 mass % in the working medium-containing composition (100 mass %).
<Heat Cycle System>

The heat cycle system of the present invention is a system employing the working medium of the present invention.

The heat cycle system may, for example, be a Rankine cycle system, a heat pump cycle system, a refrigerating cycle system or a heat transport system.
(Refrigerating Cycle System)

As an example of the heat cycle system, a refrigerating cycle system will be described.

The refrigerating cycle system is a system wherein in an evaporator, a working medium removes heat energy from a load fluid to cool the load fluid thereby to accomplish cooling to a lower temperature.

FIG. 1 is a schematic construction view illustrating an example of a refrigerating cycle system of the present invention. A refrigerating cycle system 10 is a system generally comprising a compressor 11 to compress a working medium vapor A to form a high temperature/high pressure working medium vapor B, a condenser 12 to cool and liquefy the working medium vapor B discharged from the compressor 11 to form a low temperature/high pressure working medium C, an expansion valve 13 to let the working medium C discharged from the condenser 12 expand to form a low temperature/low pressure working medium D, an evaporator 14 to heat the working medium D discharged from the expansion valve 13 to form a high temperature/low pressure working medium vapor A, a pump 15 to supply a load fluid E to the evaporator 14, and a pump 16 to supply a fluid F to the condenser 12.

In the refrigerating cyclic system 10, the following cycle is repeated.

(i) A working medium vapor A discharged from an evaporator 14 is compressed by a compressor 11 to form a high temperature/high pressure working medium vapor B.

(ii) The working medium vapor B discharged from the compressor 11 is cooled and liquefied by a fluid F in a condenser 12 to form a low temperature/high pressure working medium C. At that time, the fluid F is heated to form a fluid F', which is discharged from the condenser 12.

(iii) The working medium C discharged from the condenser 12 is expanded in an expansion valve 13 to form a low temperature/low pressure working medium D.

(iv) The working medium D discharged from the expansion valve 13 is heated by a load fluid E in an evaporator 14 to form a high temperature/low pressure working medium vapor A. At that time, the load fluid E is cooled and becomes a load fluid E', which is discharged from the evaporator 14.

Figure 2:
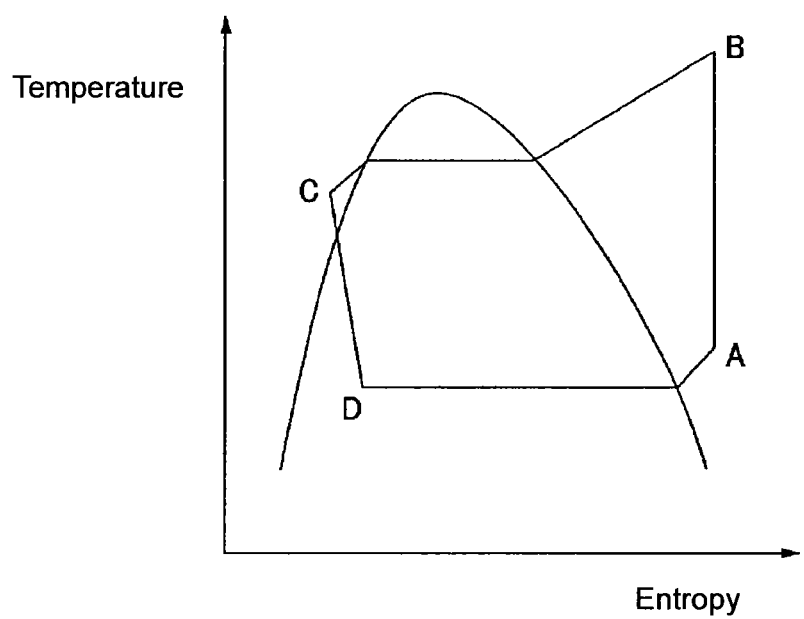
FIG. 2 is a cycle diagram illustrating the state change of a working medium in a refrigerating cycle system on a temperature-entropy chart.

The refrigerating cycle system 10 is a cycle comprising an adiabatic isentropic change, an isenthalpic change and an isobaric change, and the state change of the working medium may be shown as in FIG. 2, when it is represented on a temperature-entropy chart.

In FIG. 2, the AB process is a process wherein adiabatic compression is carried out by the compressor 11 to change the high temperature/low pressure working medium vapor A to a high temperature/high pressure working medium vapor B. The BC process is a process wherein isobaric cooling is carried out in the condenser 12 to change the high temperature/high pressure working medium vapor B to a low temperature/high pressure working medium C. The CD process is a process wherein isenthalpic expansion is carried out by the expansion valve 13 to change the low temperature/high pressure working medium C to a low temperature/low pressure working medium D. The DA process is a process wherein isobaric heating is carried out in the evaporator 14 to have the low temperature/low pressure working medium D returned to a high temperature/low pressure working medium vapor A.

Figure 3:
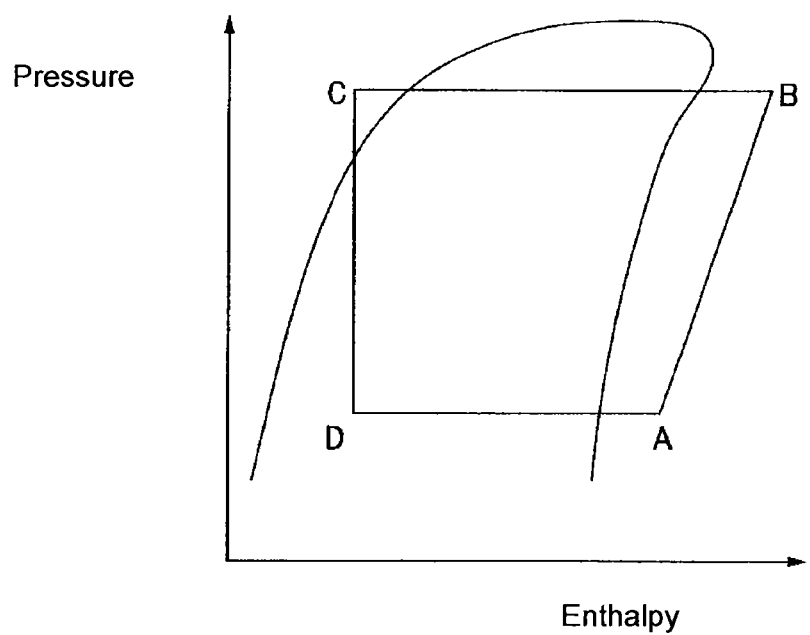
FIG. 3 is a cycle diagram illustrating the state change of a working medium in a refrigerating cycle system on a pressure-enthalpy chart.

In the same manner, the state change of the working medium may be shown as in FIG. 3, when it is represented on a pressure-enthalpy chart.
(Moisture Concentration)

There is a problem of inclusion of moisture in the heat cycle system. Inclusion of moisture may cause freezing in a capillary tube, hydrolysis of the working medium or the lubricating oil, deterioration of materials by an acid component formed in heat cycle, formation of contaminants, etc. Particularly, the above-described ether lubricating oil, ester lubricating oil and the like have extremely high moisture absorbing properties and are likely to undergo hydrolysis, and inclusion of moisture decreases properties of the lubricating oil and may be a great cause to impair the long term reliability of a compressor. Further, in an automobile air conditioner, moisture tends to be included from a coolant hose or a bearing of a compressor used for the purpose of absorbing vibration. Accordingly, in order to suppress hydrolysis of the lubricating oil, it is necessary to suppress the moisture concentration in the heat cycle system. The moisture concentration of the working medium in the heat cycle system is preferably at most 100 ppm, more preferably at most 20 ppm.

As a method of suppressing the moisture concentration in the heat cycle system, a method of using a desiccating agent (such as silica gel, activated aluminum or zeolite) may be mentioned. The desiccating agent is preferably a zeolite desiccating agent in view of chemical reactivity of the desiccating agent and the working medium, and the moisture absorption capacity of the desiccating agent.

The zeolite desiccating agent is, in a case where a lubricating oil having a large moisture absorption as compared with a conventional mineral lubricating oil is used, preferably a zeolite desiccating agent containing a compound represented by the following formula (1) as the main component in view of excellent moisture absorption capacity.

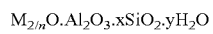     (1)

wherein M is a group 1 element such as Na or K or a group 2 element such as Ca, n is the valence of M, and x and y are values determined by the crystal structure. The pore size can be adjusted by changing M.

To select the desiccating agent, the pore size and the fracture strength are important.

In a case where a desiccating agent having a pore size larger than the molecular size of the working medium is used, the working medium is adsorbed in the desiccating agent and as a result, chemical reaction between the working medium and the desiccating agent will occur, thus leading to undesired phenomena such as formation of non-condensing gas, a decrease in the strength of the desiccating agent, and a decrease in the adsorption capacity.

Accordingly, it is preferred to use as the desiccating agent a zeolite desiccating agent having a small pore size. Particularly preferred is sodium/potassium type A synthetic zeolite having a pore size of at most 3.5 Å. By using a sodium/potassium type A synthetic zeolite having a pore size smaller than the molecular size of the working medium, it is possible to selectively adsorb and remove only moisture in the heat cycle system without adsorbing the working medium. In other words, the working medium is less likely to be adsorbed in the desiccating agent, whereby heat decomposition is less likely to occur and as a result, deterioration of materials constituting the heat cycle system and formation of contaminants can be suppressed.

The size of the zeolite desiccating agent is preferably from about 0.5 to about 5 mm, since if it is too small, a valve or a thin portion in pipelines may be clogged, and if it is too large, the drying capacity will be decreased. Its shape is preferably granular or cylindrical.

The zeolite desiccating agent may be formed into an optional shape by solidifying powdery zeolite by a binding agent (such as bentonite). So long as the desiccating agent is composed mainly of the zeolite desiccating agent, other desiccating agent (such as silica gel or activated alumina) may be used in combination.

The proportion of the zeolite desiccating agent based on the working medium is not particularly limited.

(Non-Condensing Gas Concentration)

If non-condensing gas is included in the heat cycle system, it has adverse effects such as heat transfer failure in the condenser or the evaporator and an increase in the working pressure, and it is necessary to suppress its inclusion as far as possible. Particularly, oxygen which is one of non-condensing gases reacts with the working medium or the lubricating oil and promotes their decomposition.

The non-condensing gas concentration is preferably at most 1.5 vol %, particularly preferably at most 0.5 vol % by the volume ratio based on the working medium, in a gaseous phase of the working medium.

EXAMPLES

Now, the present invention will be described in further detail with reference to Examples. However, it should be understood that the present invention is by no means restricted to such specific Examples.

(Evaluation of Refrigerating Cycle Performance)

The refrigerating cycle performance (the refrigerating capacity and the coefficient of performance) was evaluated as the cycle performance (the capacity and the efficiency) in a case where a working medium was applied to a refrigerating cycle system 10 shown in FIG. 1.

Evaluation was carried out by setting the average evaporation temperature of the working medium in an evaporator 14, the average condensing temperature of the working medium in a condenser 12, the supercooling degree of the working medium in the condenser 12, and the degree of superheat of the working medium in the evaporator 14, respectively. Further, it was assumed that there was no pressure loss in the equipment efficiency and in the pipelines and heat exchanger.

The refrigerating capacity Q and the coefficient of performance η are obtained from the following formulae (2) and (3) using the enthalpy h in each state (provided that a suffix attached to h indicates the state of the working medium).

$$Q = h_A - h_D \quad (2)$$

$$\eta = \text{refrigerating capacity/compression work} = (h_A - h_D)/(h_B - h_A) \quad (3)$$

The coefficient of performance means the efficiency in the refrigerating cycle system, and a higher coefficient of performance means that a higher output (refrigerating capacity) can be obtained by a smaller input (electric energy required to operate a compressor).

Further, the refrigerating capacity means a capacity to cool a load fluid, and a higher refrigerating capacity means that more works can be done in the same system. In other words, it means that with a working medium having a larger refrigerating capacity, the desired performance can be obtained with a smaller amount, whereby the system can be downsized.

The thermodynamic properties required for calculation of the refrigerating cycle performance were calculated based on the generalized equation of state (Soave-Redlich-Kwong equation) based on the law of corresponding state and various thermodynamic equations. If a characteristic value was not available, it was calculated employing an estimation technique based on a group contribution method.

Example 1

The refrigerating cycler performance (the refrigerating capacity and the coefficient of performance) was evaluated in a case where HCFO-1224yd, 1,1-dichloro-2,2,2-trifluoroethane (HCFC-123), 1,1,1,3,3-pentafluoropropane (HFC-245fa) or HFC-134a as a working medium was applied to a refrigerating cycle system 10 shown in FIG. 1.

The evaporation temperature of the working medium in an evaporator 14, the condensing temperature of the working medium in a condenser 12, the supercooling degree of the working medium in the condenser 12 and the degree of superheat of the working medium in the evaporator 14 were temperatures as identified in Table 1.

Based on the refrigerating cycle performance of HFC-245fa, the relative performance (each working medium/HFC-245fa) of the refrigerating cycle performance (the refrigerating capacity and the coefficient of performance) of each working medium based on HFC-245fa was obtained.

The results of each working medium are shown in Table 1.

TABLE 1

| Evaporation temperature [° C.] | Condensing temperature [° C.] | Degree of superheat [° C.] | Super-cooling degree [° C.] | Relative performance (based on HFC-245fa) [—] | | | | | | | |
|---|---|---|---|---|---|---|---|---|---|---|---|
| | | | | HCFO-1224yd | | HCFC-123 | | HFC-245fa | | HFC-134a | |
| | | | | Coefficient of performance | Refrigerating capacity | Coefficient of performance | Refrigerating capacity | Coefficient of performance | Refrigerating capacity | Coefficient of performance | Refrigerating capacity |
| 0 | 50 | 5 | 5 | 0.997 | 1.473 | 1.038 | 0.643 | 1.000 | 1.000 | 0.939 | 4.124 |
| 10 | 60 | 5 | 5 | 0.996 | 1.414 | 1.044 | 0.651 | 1.000 | 1.000 | 0.917 | 3.707 |
| 20 | 70 | 5 | 5 | 0.995 | 1.362 | 1.051 | 0.660 | 1.000 | 1.000 | 0.886 | 3.324 |
| 30 | 80 | 5 | 5 | 0.994 | 1.317 | 1.060 | 0.670 | 1.000 | 1.000 | 0.841 | 2.952 |

From the results in Table 1, it was confirmed that HCFO-1224yd had a high refrigerating capacity as compared with HFC-245fa, and had no distinct difference in the coefficient of performance.

Example 2

The refrigerating cycle performance (the refrigerating capacity and the coefficient of performance) was evaluated in a case where a working medium comprising HCFO-1224yd and a HFO as identified in Table 2 was applied to a refrigerating cycle system 10 shown in FIG. 1.

Evaluation was carried out by setting the average evaporation temperature of the working medium in an evaporator 14 to be 0° C., the average condensing temperature of the working medium in a condenser 12 to be 50° C., the supercooling degree of the working medium in the condenser 12 to be 5° C., and the degree of superheat of the working medium in the evaporator 14 to be 5° C.

Based on the refrigerating cycle performance of HFC-245fa, the relative performance (each working medium/HFC-245fa) of the refrigerating cycle performance (the refrigerating capacity and the coefficient of performance) of each working medium based on HFC-245fa was obtained. The results of each working medium are shown in Table 2.

TABLE 2

| HFO-1132(Z) [mass %] | HCFO-1224yd [mass %] | Relative performance (based on HFC-245fa) [—] | | HFO-1132(E) [mass %] | HCFO-1224yd [mass %] | Relative performance (based on HFC-245fa) [—] | | HFO-1123 [mass %] | HCFO-1224yd [mass %] | Relative performance (based on HFC-245fa) [—] | |
|---|---|---|---|---|---|---|---|---|---|---|---|
| | | Coefficient of performance | Refrigerating capacity | | | Coefficient of performance | Refrigerating capacity | | | Coefficient of performance | Refrigerating capacity |
| 0 | 100 | 0.997 | 1.473 | 0 | 100 | 0.997 | 1.473 | 0 | 100 | 0.997 | 1.473 |
| 20 | 80 | 0.997 | 2.631 | 20 | 80 | 0.994 | 2.610 | 20 | 80 | 0.980 | 2.874 |
| 40 | 60 | 0.979 | 3.558 | 40 | 60 | 0.977 | 3.516 | 40 | 60 | 0.967 | 4.302 |
| 60 | 40 | 0.960 | 4.354 | 60 | 40 | 0.959 | 4.283 | 60 | 40 | 0.902 | 5.515 |
| 80 | 20 | 0.958 | 5.121 | 80 | 20 | 0.958 | 5.012 | 80 | 20 | 0.847 | 6.873 |
| 90 | 10 | 0.959 | 5.459 | 90 | 10 | 0.960 | 5.331 | 90 | 10 | 0.839 | 7.714 |
| 92 | 8 | 0.958 | 5.520 | 92 | 8 | 0.960 | 5.389 | 92 | 8 | 0.838 | 7.886 |
| 94 | 6 | 0.958 | 5.580 | 94 | 6 | 0.960 | 5.445 | 94 | 6 | 0.838 | 8.056 |
| 96 | 4 | 0.958 | 5.637 | 96 | 4 | 0.960 | 5.499 | 96 | 4 | 0.837 | 8.222 |
| 98 | 2 | 0.958 | 5.692 | 98 | 2 | 0.960 | 5.551 | 98 | 2 | 0.836 | 8.382 |
| 100 | 0 | 0.957 | 5.746 | 100 | 0 | 0.960 | 5.601 | 100 | 0 | 0.834 | 8.536 |

From the results in Table 2, it was confirmed that the refrigerating capacity of HCFO-1224yd could be improved without a remarkable decrease of the coefficient of performance by adding a HFO to HCFO-1224yd.

Example 3

The refrigerating cycle performance (the refrigerating capacity and the coefficient of performance) was evaluated in a case where a working medium comprising HCFO-1224yd and a HCFC or a HFC as identified in Table 3 or 4 was applied to a refrigerating cycle system 10 shown in FIG. 1.

Evaluation was carried out by setting the average evaporation temperature of the working medium in an evaporator 14 to be 0° C., the average condensing temperature of the working medium in a condenser 12 to be 50° C., the supercooling degree of the working medium in the condenser 12 to be 5° C., and the degree of superheat of the working medium in the evaporator 14 to be 5° C.

Based on the refrigerating cycle performance of HFC-245fa, the relative performance (each working medium/HFC-245fa) of the refrigerating cycle performance (the refrigerating capacity and the coefficient of performance) of each working medium based on HFC-245fa was obtained. The results of each working medium are shown in Tables 3 and 4.

TABLE 3

| HCFO-1224yd [mass %] | HFC-134a [mass %] | Relative performance (based on HFC-245fa) [—] | | HCFO-1224yd [mass %] | HFC-245fa [mass %] | Relative performance (based on HFC-245fa) [—] | | HCFO-1224yd [mass %] | HFC-125 [mass %] | Relative performance (based on HFC-245fa) [—] | |
|---|---|---|---|---|---|---|---|---|---|---|---|
| | | Coefficient of performance | Refrigerating capacity | | | Coefficient of performance | Refrigerating capacity | | | Coefficient of performance | Refrigerating capacity |
| 0 | 100 | 0.939 | 4.124 | 0 | 100 | 1.000 | 1.000 | 0 | 100 | 0.746 | 6.255 |
| 20 | 80 | 0.947 | 3.726 | 20 | 80 | 0.835 | 1.410 | 20 | 80 | 0.825 | 5.253 |
| 40 | 60 | 0.959 | 3.225 | 40 | 60 | 0.986 | 1.534 | 40 | 60 | 0.910 | 4.299 |
| 60 | 40 | 0.978 | 2.697 | 60 | 40 | 1.022 | 1.611 | 60 | 40 | 0.964 | 3.347 |
| 80 | 20 | 0.988 | 2.113 | 80 | 20 | 1.020 | 1.597 | 80 | 20 | 0.982 | 2.347 |
| 100 | 0 | 0.997 | 1.473 | 100 | 0 | 0.997 | 1.473 | 100 | 0 | 0.997 | 1.473 |

TABLE 4

| HCFO-1224yd [mass %] | HFC-32 [mass %] | Relative performance (based on HFC-245fa) [—] | | HCFO-1224yd [mass %] | HFC-152a [mass %] | Relative performance (based on HFC-245fa) [—] | |
|---|---|---|---|---|---|---|---|
| | | Coefficient of performance | Refrigerating capacity | | | Coefficient of performance | Refrigerating capacity |
| 0 | 100 | 0.862 | 10.387 | 0 | 100 | 0.981 | 3.937 |
| 20 | 80 | 0.878 | 7.886 | 20 | 80 | 0.985 | 3.543 |
| 40 | 60 | 0.933 | 6.290 | 40 | 60 | 0.991 | 3.118 |
| 60 | 40 | 0.981 | 4.729 | 60 | 40 | 0.997 | 2.648 |
| 80 | 20 | 1.003 | 3.079 | 80 | 20 | 1.000 | 2.107 |
| 90 | 10 | 0.997 | 2.243 | 90 | 10 | 0.998 | 1.801 |
| 92 | 8 | 0.996 | 2.081 | 92 | 8 | 0.998 | 1.737 |
| 94 | 6 | 0.994 | 1.922 | 94 | 6 | 0.997 | 1.672 |
| 96 | 4 | 0.993 | 1.767 | 96 | 4 | 0.997 | 1.607 |
| 98 | 2 | 0.994 | 1.617 | 98 | 2 | 1.015 | 1.540 |
| 100 | 0 | 0.997 | 1.473 | 100 | 0 | 0.997 | 1.473 |

From the results in Tables 3 and 4, it was confirmed that the refrigerating capacity of HCFO-1224yd could be improved by adding a HFC to HCFO-1224yd.

Example 4

The refrigerating cycle performance (the refrigerating capacity and the coefficient of performance) was evaluated in a case where a working medium comprising HCFO-1224yd and a hydrocarbon as identified in Table 5 was applied to a refrigerating cycle system 10 shown in FIG. 1.

Evaluation was carried out by setting the average evaporation temperature of the working medium in an evaporator 14 to be 0° C., the average condensing temperature of the working medium in a condenser 12 to be 50° C., the supercooling degree of the working medium in the condenser 12 to be 5° C., and the degree of superheat of the working medium in the evaporator 14 to be 5° C.

Based on the refrigerating cycle performance of HFC-245fa, the relative performance (each working medium/HFC-245fa) of the refrigerating cycle performance (the refrigerating capacity and the coefficient of performance) of each working medium based on HFC-245fa was obtained. The results of each working medium are shown in Table 5.

refrigerating capacity and the coefficient of performance) of each working medium based on HCFC-123 was obtained. The results of each working medium are shown in Table 6.

TABLE 6

| | Relative performance (based on HCFC-123) [—] | |
|---|---|---|
| | Refrigerating capacity | Coefficient of performance |
| HCFO-1224yd | 1.78-2.42 | 0.91-0.97 |
| HCFC-123 | 1 | 1 |
| HCFO-1233zd(E) | 1.27-1.47 | 0.98-1.00 |

From the results in Table 6, it was confirmed that HCFO-1224yd had a high refrigerating capacity as compared with HCFO-1233zd(E), and had no distinct difference in the coefficient of performance.

INDUSTRIAL APPLICABILITY

The working medium of the present invention is useful as a working medium for heat cycle such as a coolant for a refrigerator, a coolant for an air conditioner, a working fluid

TABLE 5

| HCFO-1224yd [mass %] | Butane [mass %] | Relative performance (based on HFC-245fa) [—] | | HCFO-1224yd [mass %] | Isobutane [mass %] | Relative performance (based on HFC-245fa) [—] | | HCFO-1224yd [mass %] | Propane [mass %] | Relative performance (based on HFC-245fa) [—] | |
|---|---|---|---|---|---|---|---|---|---|---|---|
| | | Coefficient of performance | Refrigerating capacity | | | Coefficient of performance | Refrigerating capacity | | | Coefficient of performance | Refrigerating capacity |
| 0 | 100 | 1.000 | 1.621 | 0 | 100 | 0.975 | 2.229 | 0 | 100 | 0.917 | 5.528 |
| 20 | 80 | 1.094 | 1.639 | 20 | 80 | 0.990 | 2.196 | 20 | 80 | 0.919 | 5.062 |
| 40 | 60 | 0.934 | 1.654 | 40 | 60 | 0.991 | 2.137 | 40 | 60 | 0.926 | 4.484 |
| 60 | 40 | — | — | 60 | 40 | 0.991 | 2.031 | 60 | 40 | 0.948 | 3.792 |
| 80 | 20 | 1.014 | 1.617 | 80 | 20 | 1.007 | 1.840 | 80 | 20 | 0.976 | 2.868 |
| 90 | 10 | 1.012 | 1.566 | 90 | 10 | 0.994 | 1.688 | 90 | 10 | 0.981 | 2.229 |
| 92 | 8 | 1.019 | 1.552 | 92 | 8 | 0.997 | 1.651 | 92 | 8 | 0.981 | 2.085 |
| 94 | 6 | 1.025 | 1.535 | 94 | 6 | 1.001 | 1.611 | 94 | 6 | 0.981 | 1.936 |
| 96 | 4 | 1.021 | 1.517 | 96 | 4 | 1.006 | 1.569 | 96 | 4 | 0.983 | 1.783 |
| 98 | 2 | 1.032 | 1.497 | 98 | 2 | 1.017 | 1.523 | 98 | 2 | 1.016 | 1.629 |
| 100 | 0 | 0.997 | 1.473 | 100 | 0 | 0.997 | 1.473 | 100 | 0 | 0.997 | 1.473 |

From the results in Table 5, it was confirmed that the refrigerating capacity of HCFO-1224yd could be improved without a remarkable decrease of the coefficient of performance by adding a hydrocarbon to HCFO-1224yd.

Example 5

The refrigerating cycle performance (the refrigerating capacity and the coefficient of performance) was evaluated in a case where HCFO-1224yd, HCFC-123 or HCFO-1233zd(E) as a working medium was applied to a refrigerating cycle system 10 shown in FIG. 1.

Evaluation was carried out by setting the average evaporation temperature of the working medium in an evaporator 14 to be from −10 to +50° C., the average condensing temperature of the working medium in a condenser 12 to be the average evaporation temperature +50° C., the supercooling degree of the working medium in the condenser 12 to be 5° C., and the degree of superheat of the working medium in the evaporator 14 to be 5° C.

Based on the refrigerating cycle performance of HCFC-123, the relative performance (each working medium/HCFC-123) of the refrigerating cycle performance (the for power generation system (such as exhaust heat recovery power generation), a working medium for a latent heat transport apparatus (such as a heat pipe) or a secondary cooling medium.

This application is a continuation of PCT Application No. PCT/JP2012/062842, filed on May 18, 2012, which is based upon and claims the benefit of priority from Japanese Patent Application No. 2011-112415 filed on May 19, 2011. The contents of those applications are incorporated herein by reference in its entirety.

REFERENCE SYMBOL

10: Refrigerating cycle system

What is claimed is:
1. A working medium composition comprising 1-chloro-2,3,3,3-tetrafluoropropene and a dibasic acid ester oil.
2. The working medium composition according to claim 1, which further comprises a stabilizer.
3. The working medium composition according to claim 2, wherein a content of the stabilizer is at most 5 mass % in 100 mass % of the working medium composition.

4. The working medium composition according to claim 1, which further comprises a leak detecting substance.

5. The working medium composition according to claim 4, wherein the leak detecting substance is an ultraviolet fluorescent dye, an odor gas or an odor masking agent.

6. The working medium composition according to claim 4, wherein a content of the leak detecting substance is at most 2 mass % in 100 mass % of the working medium composition.

7. The working medium composition according to claim 1, which further comprises 1,1,2-trifluoroethylene.

8. A heat cycle system comprising the working medium composition of claim 1.

9. A heat cycle system comprising the working medium composition of claim 7.

10. The working medium composition according to claim 1, comprising 1-chloro-2,3,3,3-tetrafluoropropene and ditridecyl glutarate.

11. The working medium composition according to claim 1, comprising 1-chloro-2,3,3,3-tetrafluoropropene and an ester of a $C_{5-10}$ dibasic acid with a $C_{1-15}$ monohydric alcohol which is linear or has a branched alkyl group.

12. The working medium composition according to claim 1, comprising 1-chloro-2,3,3,3-tetrafluoropropene and di(2-ethylhexyl) adipate.

13. The working medium composition according to claim 1, comprising 1-chloro-2,3,3,3-tetrafluoropropene and diisodecyl adipate.

14. The working medium composition according to claim 1, comprising 1-chloro-2,3,3,3-tetrafluoropropene and ditridecyl adipate.

15. The working medium composition according to claim 1, comprising 1-chloro-2,3,3,3-tetrafluoropropene and di(3-ethylhexyl) sebacate.

* * * * *